(12) United States Patent
Crandall

(10) Patent No.: US 6,333,057 B1
(45) Date of Patent: Dec. 25, 2001

(54) COMPOSITION AND METHOD FOR TOPICAL TREATMENT OF ANDROGENIC ALOPECIA

(76) Inventor: Wilson T. Crandall, Rte. 616, Jolly Hill, Ft. Defiance, VA (US) 24437

( * ) Notice: Subject to any disclaimer, the term of this patent is extended or adjusted under 35 U.S.C. 154(b) by 0 days.

(21) Appl. No.: 09/116,851

(22) Filed: Jul. 16, 1998

Related U.S. Application Data

(63) Continuation of application No. 08/676,095, filed on Jul. 2, 1996, now abandoned.
(60) Provisional application No. 60/000,842, filed on Jul. 3, 1995, and provisional application No. 60/005,643, filed on Oct. 19, 1995.

(51) Int. Cl.$^7$ ..................................................... A61K 35/78
(52) U.S. Cl. ..................... 424/727; 424/70.1; 424/450; 424/484; 424/489; 514/78; 514/170; 514/690; 514/880; 514/930; 514/944; 514/946; 514/951; 514/959; 514/961
(58) Field of Search .............................. 424/195.1, 70.1, 424/94.1, 450, 484, 489, 727; 514/78, 170, 690, 880, 936, 944, 946, 951, 959, 961

(56) References Cited

U.S. PATENT DOCUMENTS

| | | |
|---|---|---|
| 3,062,721 | 11/1962 | Grate . |
| 3,905,869 | 9/1975 | Hidaka et al. . |
| 3,932,618 | 1/1976 | Fujii et al. . |
| 3,952,099 | 4/1976 | Smith . |
| 4,343,816 * | 8/1982 | Cavazza .............................. 424/316 |
| 4,507,286 | 3/1985 | Vellini . |
| 4,689,345 | 8/1987 | Kasha et al. . |
| 4,701,471 | 10/1987 | Loucks, Sr. et al. . |
| 4,760,096 | 7/1988 | Sakai et al. . |
| 4,783,450 | 11/1988 | Fawzi et al. . |
| 4,855,322 | 8/1989 | Kasha et al. . |
| 4,863,898 | 9/1989 | Ashmead et al. . |
| 4,935,240 | 6/1990 | Nakail et al. . |
| 5,053,403 | 10/1991 | Orentreich et al. . |
| 5,116,605 | 5/1992 | Alt . |
| 5,178,879 | 1/1993 | Adekunle et al. . |
| 5,238,933 | 8/1993 | Catz et al. . |
| 5,254,338 | 10/1993 | Sakai et al. . |
| 5,264,619 | 11/1993 | Ford . |
| 5,314,689 | 5/1994 | Scandurra et al. . |
| 5,340,579 | 8/1994 | Casero . |
| 5,352,438 | 10/1994 | N'Guyen et al. . |
| 5,382,431 | 1/1995 | Pickart . |
| 5,554,375 | 9/1996 | Pickart . |
| 5,560,910 | 10/1996 | Crandall . |

FOREIGN PATENT DOCUMENTS

| | | |
|---|---|---|
| 370379 * | 5/1990 | (EP) . |
| 0 370 379A1 | 5/1990 | (EP) . |
| 2 643 375A1 | 8/1990 | (FR) . |
| 52099223 * | 8/1977 | (JP) . |
| 01216912 * | 8/1989 | (JP) . |

OTHER PUBLICATIONS

Mellin et al., J. Steroid Biochem. Molec. Biol. 44(2): 121–131 (1993).*
Vacher et al., J. Biomed Sci 2: 357–365 (1995).*
Redmond et al., Cleveland Clinic Journal of Medicine 57(5): 428–0432 (Jul.–Aug. 1990).*
Olsen et al., Journal of the American Academy of Dermatology 23(3, Part 1): 470472 (Sep. 1990).*
Rushton et al., Clinical and Experimental Dermatology 14: 40–46 (1989).*
Taussig, S.J., "The Mechanism of the Physiological Action of Bromelain", *Medical Hypothesis*, vol. 6, pp. 99–104 (1980).
Choi, Hoo–Kyun, et al., "Transdermal Delivery of Bioactive Peptides: The Effect of n–Decylmethyl Sulfoxide, pH, and Inhibitors on Enkephalin Metabolism and Transport", *Pharm. Res.*, vol. 7, No. 11, pp. 1099–1106, (1990).
Hoo–Kyun, C. et al., "Some General Influences of n–Decylmethyl Sulfoxide on the Permeation of Drugs Across Hairless Mouse Skin", *J. Invest, Derm.*, vol. 96, pp. 822–826 (1991).
Smith, E. W., Maibach, H. eds., *Percutaneous Penetration Enhancers*, CRC Press, p. 109–113 (1995).
Colpaert et al., "Effects of Capsaicin on Inflammation and on the Substance P Content of Nervous Tissues in Rats with Adjuvant Arthritis," *Life Sciences*, vol. 32, pp. 1827–1834 (1983).
Lam et al., "Capsaicin Suppresses Substance P–Induced Joint Inflammation in the Rat," *Neuroscience Letter*, 105, pp. 155–158 (1989).
Lee et al., "Relationship Between Lipophilicity and Skin Permeability of Various Drugs from an Ethanol/Water/Lauric Acid System", *Biol. Pharm. Bull.*, vol. 17, No. 10, pp. 1421–1424 (1994).

* cited by examiner

Primary Examiner—Jean C. Witz

(57) ABSTRACT

This invention relates to the topical and oral treatment of hair loss, especially androgenic alopecia, by providing formulations that include anti-androgens, especially extracts of the saw palmetto plant, co-enzyme Q, and acetyl carnitine, and optionally stimulators of adenylate cyclase to stimulate hair growth, to increase the luster of hair, and to decrease hair graying.

7 Claims, No Drawings

COMPOSITION AND METHOD FOR TOPICAL TREATMENT OF ANDROGENIC ALOPECIA

PRIOR RELATED APPLICATIONS

This application is a continuation of U.S. patent application Ser. No. 08/676,095, filed on Jul. 2, 1996, now abandoned, which claims priority to United States provisional Patent Applications Serial Numbers 60/000,842 and 60/005,643 filed on Jul. 3, 1995 and Oct. 19, 1995, respectively.

TECHNICAL FIELD OF THE INVENTION

This invention relates to the topical and oral treatment of hair loss, especially androgenic alopecia, by providing formulations that include anti-androgens, especially extracts of the saw palmetto plant, co-enzyme Q, and acetyl carnitine, and optionally stimulators of adenylate cyclase, to stimulate hair growth, to increase the luster of hair, and to decrease hair graying.

BACKGROUND OF THE INVENTION

Androgenic alopecia is an autosomal disorder which begins in puberty in genetically disposed individuals. Androgenic alopecia is also known as hereditary baldness, male pattern baldness, and seborrheic alopecia and occurs in males and females. The disorder is heterogeneous and increased circulating androgens are not the only causative factor. Historically, patients with male androgenic alopecia present with frontal recession of the hairline, especially at the temples and vertex, and androgenetic frontal hairline (incipient regression of terminal hairs into shorter thin hairs of the intermediate and vellous type). Minoxidil, available since 1988, produces a maximum of only 40% cosmetic responses in selected patients with vertex balding who are young, recently diagnosed and display small areas of alopecia. The response to minoxidil is not seen for 4 to 10 months and treatment must be maintained or the hairline regresses.

Saw palmetto is a small, creeping palm (*Serenoa repens*) of the southeastern United States, having palmately divided leaves with one-ribbed segments and black, one-seeded fruit. It is a native American tree of South Carolina and Georgia and extracts of this tree have been used successfully to treat benign prostatic hypertrophy. Extracts of saw palmetto act as a multi-site inhibitor of the hormone dihydrotestosterone (DHT) which is responsible for prostatic hypertrophy. Saw palmetto blocks approximately 50% of the binding of DHT to receptors in the prostate. It also blocks the uptake of DHT into the nucleus of prostatic cells, and strongly inhibits the action of the enzyme testosterone 5 alpha-reductase which reduces the conversion of testosterone to DHT.

Methods and compositions for increasing the growth of hair are needed, especially in situations of hair loss due to androgenic alopecia. One composition should be easy to apply topically and should promote hair growth. Another composition should be orally administered and promote hair growth.

SUMMARY OF THE INVENTION

In one embodiment, the present invention provides an easy to use topical therapeutic composition and treatment for increasing the growth of hair.

In another embodiment, the present invention provides a therapeutic composition and oral treatment for increasing the growth of hair and the luster of hair, and for decreasing the graying of hair.

Accordingly, it is an object of the present invention to provide a treatment for hair loss through the topical application of anti-androgens in various formulations designed for topical application.

It is an object of the present invention to provide a treatment for hair loss through the topical application of extracts of saw palmetto, which act as anti-androgens, in various formulations designed for topical application.

Another object of the invention to provide a treatment for hair loss through the oral application of anti-androgens in various formulations designed for oral application, combined with co-enzyme Q and acetyl carnitine.

It is another object of the invention to provide a treatment for hair loss through the oral application of saw palmetto extracts in various formulations designed for oral application, combined with co-enzyme Q and acetyl carnitine.

Another object of the invention to provide a treatment for hair loss through the oral application of saw palmetto extracts in various formulations designed for oral application, combined with co-enzyme Q, acetyl carnitine, and stimulators of adenylate cyclase.

Still another object of the invention is to provide a composition and treatment for hair loss through the topical application of anti-androgens combined with co-enzyme Q and acetyl carnitine in various formulations designed for topical application.

Another object of the invention is to provide a composition and treatment for hair loss through the topical application of anti-androgens combined with stimulators of adenylate cyclase, co-enzyme Q and acetyl carnitine in various formulations designed for topical application.

Still another object of the invention is to provide a composition and treatment for hair loss through the topical application of extracts of saw palmetto combined with co-enzyme Q and acetyl carnitine in various formulations designed for topical application.

These and other objects, features and advantages of the present invention will become apparent after a review of the following detailed description of the disclosed embodiments.

DETAILED DESCRIPTION OF THE INVENTION

The following United States provisional Patent Applications are incorporated by reference herein in their entirety, Serial Numbers 60/000,842 and 60/005,643 filed on Jul. 3, 1995 and Oct. 19, 1995, respectively.

The term "saw palmetto" refers to a native American tree often found in the southeastern part of the United States, especially in Georgia and Florida. As used in the present context, the term "saw palmetto" includes extracts of the saw palmetto tree. These extracts may be present as oil extracts among other forms.

The term "androgen" refers to testosterone and its precursors and metabolites, and 5-alpha reduced androgens, including but not limited to dihydrotestosterone. Androgen refers to androgens from the testis, adrenal gland, and ovaries, as well as all forms of natural, synthetic and substituted or modified androgens.

It is to be understood that other agents which affect the synthesis, metabolism, site of action, and function of androgens are considered within the scope of the present invention when combined with acetyl carnitine and co-enzyme Q. Included within the scope of this invention are drugs, extracts, chemicals, or other agents which affect the biosynthesis, enzymatic conversion, binding to receptors, and metabolism of androgens. Agents which modify the translocation of androgens to the nucleus or the second messenger systems that transduce intracellular signals are also considered within the scope of this invention when combined with acetyl carnitine and co-enzyme Q. Agents which affect the synthesis, release, and function of hypothalamic and pituitary hormones which affect the synthesis or release of testosterone are also included in the scope of this invention when combined with acetyl carnitine and co-enzyme Q for stimulating hair growth. Accordingly, methods for stimulating hair growth which employ acetyl carnitine and co-enzyme Q combined with agents described in this paragraph which affect the synthesis, release, efficacy, or metabolism of androgens are considered within the scope of this invention. Accordingly, molecules which affect hypothalamic synthesis and secretion of gonadotropin releasing hormone (GnRH), GnRH agonists (such as leuprolide and gonadorelin) which affect pituitary release of gonadotropins, ketoconazole and liarazole which affect testosterone synthesis in the testis, finasteride and saw palmetto extract which affect conversion of testosterone to dihydrotestosterone by 5-alpha reductase in its various forms in extraglandular tissues, and flutamide and cyproterone acetate which affect binding of androgen to its receptor, are all considered within the scope of this invention. The aforementioned molecules in this paragraph are collectively defined as "antiandrogens" within this application.

The term "androgenic alopecia" refers to an autosomal disorder which begins in puberty in genetically disposed individuals. Androgenic alopecia is also known as hereditary baldness, male pattern baldness, and seborrheic alopecia. Androgenic alopecia may occur in males and females.

The term "acetyl carnitine" refers to various forms of acetyl carnitine, including but not limited to, D,L-carnitine, and acetyl-L-carnitine hydrochloride which is usually employed in a 1% to 5% solution. Acetyl carnitine (PCAA, Houston, Tex.) is thought to decrease in senescence and down regulation. Although not wanting to be bound by this statement, it is believed that the decrease in acetyl carnitine compromises the transport of fatty acids from the cytosol into the inner mitochondrial membrane of the mitochondria, thereby impairing the physiological function of the follicle, perhaps through effects on fatty acid oxidation and ATP production. Acetyl carnitine is believed to improve fatty acid metabolism by stimulation of cardiolipin which affects the activity of the inner mitochondrial membrane, affecting its permeability and function for proton transport. Acetyl carnitine is also believed to synergize with co-enzyme Q in the revitalization of senescent hair follicles.

The term "co-enzyme Q" refers to several forms of co-enzyme Q including co-enzyme Q0, co-enzyme Q2, co-enzyme Q6, co-enzyme Q7, co-enzyme Q9 and co-enzyme Q 10, and are all considered within the scope of this invention. Several of these forms are also known as ubiquinones and may be obtained from PCAA (Houston, Tex.). Various forms of co-enzyme Q (PCAA, Houston, Tex.) are utilized because it is believed that the senescent hair follicles are metabolically reduced through reduced activity of respiratory enzymes. Although not wanting to be bound by this statement, it is believed that co-enzyme Q, especially co-enzyme Q10, increases respiratory levels compatible with hair formation. Although not wishing to be bound by this statement, it is believed that supplementation with co-enzyme Q facilitates removal of excess protons accumulated at the inner mitochondrial membrane due to prolonged down regulation, acts as an antioxidant, and promotes normalization of oxidative function (Shigenaga, M. et al. Proc. Soc. Natl. Acad. Sci. USA 99: 10771–10778, 1994).

The term "lecithin" is used to mean a phosphatide called phosphatidylcholine and can be isolated from soybean, eggs and other sources including, but not limited to, heart, brain, and liver. Lecithin is a mixture of the diglycerides of stearic, palmitic, and oleic acids, linked to the choline ester of phosphoric acid. Soybean lecithin is a preferred lecithin and may contain the following acids; palmitic, stearic, palmitoleic, oleic, linoleic, linolenic and arachidonic as described in the *Merck Index* (Ninth edition, 1976, page 711).

The term "PLURONIC" refers to poloxamer compounds and are sold collectively under the trademark PLURONIC (BASF, Parsippany, N.J.). PLURONIC F-127 corresponds to poloxamer 407, a polyoxypropylene/polyoxyethylene block copolymer described by Schmolka in the *Journal of Biomedical Materials Research* 6: 571–582, (1972). As used in this application, the terms PLURONIC organogel, poloxamer organogel, and polyoxyethylene/polyoxypropylene organogel are synonymous.

"Topical" application is used to mean local administration of the composition and its various embodiments, for example, in the treatment of alopecia. The composition according to the present invention can be in the form of solutions, lotions, salves, creams, ointments, liposomes, sprays, gels, roller sticks or any other method using micelles and pharmaceutically acceptable penetration enhancers. In one embodiment, the composition may be applied to the scalp at bedtime and again after showering in the morning for a total of two applications per day.

The "enhanced penetration" caused by compositions of this invention as used in topical application with this method, means increased penetration into the skin, and is achieved with compounds such as lecithin organogel, PLURONIC organogel (BASF, Parsippany, N.J.), N-decylmethyl sulfoxide (NDMS), and ethoxydiglycol:ethanol, and can be observed in many ways known to those skilled in the art.

"Oral administration" refers to the administration of the compositions of the present invention into the gastrointestinal tract in any form, including but not limited to the following, tablets, powders, suspensions, solutions, lozenges, and lollipops.

The present invention includes a composition for topical treatment of androgenic alopecia comprising antiandrogens, including but not limited to saw palmetto extracts, combined with co-enzyme Q and acetyl carnitine. These compounds are delivered topically combined with delivery vehicles and penetrating agents optionally containing lecithin, isopropyl palmitate, lecithin organogel, PLURONIC F-127 organogel, NDMS, ethoxydiglycol:ethanol and/or water. When co-enzyme Q is used in the absence of organogels, it is first dissolved in ethoxydiglycol:ethanol and then in Tween, such as Tween 20 or Tween 80, glycerol, castor oil, olive oil, or another appropriate agent. For example, these agents are useful in the formation of the composition of the present invention as a roller for topical application.

In one embodiment, therapeutically effective amounts of the following compounds may be combined at the indicated concentrations expressed per 120 ml of formulation for topical application: saw palmetto (1 g to 20 g), co-enzyme Q (0.1 g to 10 g), and acetyl carnitine (0.1 g to 20 g).

Preferred concentrations of these compounds for use in topical application are provided in Example 4.

Another preferred penetrating agent and delivery vehicle is lecithin organogel which is a combination of lecithin, isopropyl pannitate and water. Lecithin organogels have been described as vehicles that are useful in facilitating the delivery of low molecular weight compounds transdermally (Willimann, H., et al., "Lecithin Organogel as Matrix for Transdermal Transport of Drugs", *J. Pharm. Sci.*, Vol. 81, 1992, which is incorporated herein by reference). The lecithin organogels are obtained by adding small amounts of water to a solution of lecithin in organic solvents. Generally, lecithin organogels are prepared at room temperature by first dissolving lecithin in an organic solvent such as isopropyl palmitate and then adding enough water while stirring to obtain the desired gel. Preparation of a variety of lecithin gels, all of which are appropriate in practicing the present invention, are described in Scartazzini, et al. *Journal of Physical Chemistry*, Vol. 92, pgs. 829–833 (1988) and Luisi, P. L. et al. *Colloid and Polymer Science*, Vol. 268, pgs. 356–374 (1990), both of which are incorporated herein by reference. The lecithin organogel preferably comprises 1:1 to 1.5:5 (weight/vol) of soy lecithin (PCAA, Kinghurst, Houston, Tex.) to isopropyl palmitate (PCAA) (1 g:1 ml). Other penetrating agents may be used in the composition of the present invention.

The formation of organogels containing lecithin dissolved with isopropyl palmitate or other solvents, and water, has been described by Luisi et al., *Colloid and Polymer Science* 268: 356–374 (1990) and Scartazzini et al., *The Journal of Physical Chemistry* 92: 829–833 (1988). Willimann et al., *Journal of Pharmaceutical Sciences* 81:871–874 (1992), examined the efficacy of lecithin organogels for use in the transdermal delivery of drugs such as scopolamine and broxaterol. Willimann et al., also observed that lecithin organogels had no detrimental effect on skin when compared to control samples treated with physiological saline (see page 872, column 2, paragraph 3, *Journal of Pharmaceutical Sciences* 81:871–874 (1992)).

The present invention optionally includes lecithin (20% –98%) dissolved with isopropyl palmitate or other solvents in combination with an approximately 10% –20% solution of PLURONIC F-127 (BASF, Parsippany, N.J.), otherwise known as poloxamer 407, in a ratio of approximately 1:3 to 1:4. This ratio may be varied by one of ordinary skill in the art. Other PLURONICS may be used in the present invention. It is to be understood that the soy lecithin of the present invention is a preferred lecithin source and may be dissolved in isopropyl palmitate to achieve a final concentration in the composition of from approximately 20% –98%, with a more preferred final concentration of from approximately 20%–40%. Lecithins may optionally be derived from eggs, and organs such as heart, brain, and liver, and used at concentrations of approximately 20%–99%, with more preferred final concentrations of from approximately 20%–40%. The composition according to the present invention can be in the form of lotions, salves, creams, ointments, liposomes, sprays, micelles, or gels. The desired form is lotions, ointments and salves. Liposomes are described in detail by Oleniacz in U.S. Pat. No. 3,957,971, the entirety of which is hereby incorporated by reference.

Another delivery vehicle is n-Decylmethyl sulfoxide (NDMS obtained from PCAA 10925). NDMS is optionally present at a concentration of between approximately 0.01% and 1% by weight, with a preferred concentration of between approximately 0.05% and 0.5% by weight, with the most preferred concentration of approximately 0.125% by weight. NDMS is dissolved in 10 ml of a 75% solution of ethanol. Next, acetyl carnitine is dissolved in purified water. Co-enzyme Q is added to 2 to 5 ml of ethoxydiglycol and then to 10 ml of 70% ethanol plus Tween 80. Finally, purified water is added to a final volume of 120 ml.

A gelling agent optionally may be added to the formulation. Gelling agents that are suitable for use in the present invention include, but are not limited to, cellulose, cellulose ethers, carboxymethylcellulose, alginates, polyacrylates, bentonite, gelatin, tragacanth, polyvinylpyrrolidone, polyvinyl alcohol, and polyoxyethylene/polyoxypropylene block copolymers, some of which are known as poloxamers. The poloxamer compounds are sold collectively under the trademark PLURONIC (BASF, Parsippany, N.J.). PLURONIC F-127 corresponds to poloxamer 407. Other PLURONICS may be used in the present invention. As used in this application, the terms PLURONIC organogel, poloxamer organogel and polyoxyethylene/polyoxypropylene organogel are synonymous.

A preservative, such as benzyl alcohol (1%) or potassium sorbate, may be added to the composition. An antioxidant, including but not limited to antioxidants such as vitamin E, proanthocyanidin, or lipoic acid, may be added to lecithin organogels and PLURONIC organogels. Other preservatives well known to those of ordinary skill in the art can be used in the composition.

Agents for improving the aroma of the formulation for topical application can optionally be added to the composition. A desired aroma improving agent is honey almond oil (PCAA). Other aroma improving agents include, but are not limited to, avocado oil, sesame oil, castor oil, olive oil, grapeseed oil, clove oil, groundnut oil, corn oil, lemon oil, coconut oil, lime oil, hazelnut oil, jojoba oil, carthamus oil and wheatgerm oil. The oils can be added individually or in combination. It is to be understood that various fragrances and assorted floral scents may be optionally added to the composition and are commercially available (PCAA). Stabilizers, antioxidants, preservatives, humectants, regreasing agents, solvents or auxiliaries can be added to improve stability and/or adhesiveness of the formulations. Cosmetic agents such as panthenol may also optionally be added to the formulation.

In addition, antimicrobial agents can be optionally added to the composition of the present invention. Addition of an antimicrobial agent is desirable when treating inflammatory conditions associated with loss of hair.

The composition of the present invention can be administered topically twice daily or several times per day depending upon the nature and severity of the condition being treated. The lecithin organogel or PLURONIC organogel may be wiped off about 1 hour after application if desired since the active ingredients are absorbed rapidly.

The present invention also includes formulations for the treatment of androgenic alopecia that may be administered orally. These formulations for oral administration do not contain penetration enhancers such as NDMS or lecithin organogel. The present invention includes a composition for oral treatment of androgenic alopecia comprising anti-androgens such as saw palmetto extracts combined with co-enzyme Q and acetyl carnitine. Typical concentration ranges for these compounds used in oral administration are the following; saw palmetto (10 mg –1 g), co-enzyme Q (10 mg –250 mg), and acetyl carnitine (250 mg –2 g). A preferred composition for administration as a pill into the oral cavity twice daily, at approximately 12 hour intervals, is saw palmetto (160 mg), co-enzyme Q10 (30 m–180 mg), and acetyl carnitine (1 g). These compounds for oral administration are delivered into the gastrointestinal tract in any form, including but not limited to the following; tablets, powders, suspensions, solutions, lozenges, lollipops, through catheters, and various tubes, including but not limited to nasogastric, gastric, duodenal, jejeunal, ileal and colonic tubes. When administered into the oral cavity, various compounds may be added to improve the flavor and consistency of the composition. For example, the composition could be administered into the oral cavity in the form of a cherry flavored lozenge, or a grape flavored syrup.

While not wanting to be bound by this statement, it is believed that DHT affects adenylate cyclase in the hair follicle, thereby modulating keratin production and affecting hair quality and formation. Accordingly, it is within the scope of this invention to include stimulators of adenylate cyclase in conjunction with anti-androgens to stimulate activity of the hair follicle and increase hair growth. In one embodiment, the drug forskolin, a stimulator of adenylate cyclase, is combined with anti-androgens, such as saw palmetto extracts, co-enzyme Q and acetyl carnitine, and a penetrant for topical application. For topical application, a concentration of about 0.1% to 10% may be used with a preferred concentration of 1% to 5% forskolin per 120 ml of formulation. In oral preparations, forskolin is included at a concentration of about 0.2 mg to 100 mg, with a preferred concentration of about 2 mg to 20 mg, together with anti-androgens, such as saw palmetto extracts, co-enzyme Q and acetyl carnitine. It is understood that these dosages of forskolin are preferred dosages and that other dosages may suggest themselves to those skilled in the art. Similarly, other stimulators of adenylate cyclase will be administered at dose ranges specific for each stimulator.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention.

Example 1

Topical Application of Saw Palmetto Extracts Increase Hair Growth in Males with Alopecia A 52 year old male at the first recognition of alopecia at the temples and frontal recession of the hairline applied the formulation of the present invention as described below. The composition consisting of the formulation of saw palmetto, co-enzyme Q and acetyl carnitine was used in PLURONIC organogel and NDMS twice a day at the right (R) triangulus for a period of 3 weeks. One morning, large numbers of vellous hairs were evident. Treatment was then extended to the left (L) triangulus where vellous hair growth also occurred. The frontal scalp line was treated with the formulation for a period of 3–4 weeks and intermediate hairs were observed among the anagen hairs. The hair was decisively more mature in appearance. Analysis of root hairs of the frontal scalp line indicated an marked increase in the percent of telogen follicles to 35% from the normal 20% and an increase in the percent of catogen follicles.

Five individual volunteers from 52 to 56 years of age and another three individual volunteers from 31 to 38 years of age were treated with the topical application of saw palmetto extracts in the composition described in the preceding paragraph. Alopecia in these individuals varied from a rating of Hamilton 2 to Hamilton 8. Totally bald scalp devoid of pigmented hair from 5 to 25 years responded to the disclosed treatment of this invention in an interval of time directly correlated with age, rapidity of hair loss and duration of baldness. In general terms, younger men who were bald for less time responded to the treatment faster than individuals such as older men who were bald for longer periods. Photographs of the scalp of these individuals verified increased hair growth.

Example 2

Lecithin Organogel Composition Prepared With Pluronic

A preferred composition for delivery of the formulation of saw palmetto, co-enzyme Q and acetyl carnitine was prepared as described below. The lecithin organogel was prepared by dissolving 20 g of soy lecithin granules (PCAA) in 20 ml of isopropyl palmitate (PCAA). The mixture was stirred periodically for 24 hours until the soy lecithin granules were dissolved. The PLURONIC gel 20% stock solution was prepared by dissolving 16 g of PLURONIC F127 powder (BASF, Parsippany, N.J.), also called poloxamer 407, in 80 ml of purified water. Potassium sorbate (160 mg; PCAA) was added to the PLURONIC gel 20% stock solution as a preservative. This was placed in the refrigerator at about 4° C. for about 24 hours and stirred periodically.

The composition was prepared by mixing 20 ml of the lecithin organogel with 2 ml of the honey almond oil (PCAA) until a smooth mixture was prepared. Honey almond oil was added for fragrance. Next, 80 ml of the PLURONIC gel 20% stock solution was mixed in until a gel formed. A blender was used for this mixing step at room temperature with disinfected equipment. The gel was stored at room temperature.

Example 3

Lecithin Organogel Composition Prepared Without Pluronic

In another embodiment of the present invention for delivery of the formulation, the composition described in Example 2 was prepared using lecithin organogel without the addition of the PLURONIC gel 20% stock solution. The final concentration of lecithin organogel was in the range of 20–45 % by modifying the ratio of lecithin organogel to water.

Example 4

Compositions For The Topical Treatment Of Androgenic Alopecia

Extracts of saw palmetto are added at a concentration of 5 g to 7.5 g per 120 ml of formulation to the compositions of Examples 2 and 3 in effective therapeutic concentrations. Next, therapeutically effective amounts of co-enzyme Q10 (0.5 g to 1 g per 120 ml of formulation) and acetyl carnitine (1 g to 2 g per 120 ml of formulation) are added to this mixture of saw palmetto in the compositions of Examples 2 and 3 to create the formulation for topical treatment of alopecia.

Example 5

Compositions And Methods For The Treatment Of Androgenic Alopecia By Oral Administration A composition for treatment of androgenic alopecia by oral administration comprises saw palmetto extracts (160 mg), combined with the following components selected from the group comprising co-enzyme Q10 (30 mg to 180 mg) and acetyl carnitine (1 gm).

These compounds are usually delivered twice daily into the gastrointestinal tract in forms including, but not limited to the following; tablets, powders, suspensions, solutions, lozenges, and lollipops, and also through catheters, and various tubes, including but not limited to nasogastric, gastric, duodenal, jejeunal, ileal and colonic tubes. These compounds are delivered into the oral cavity in the form of tablets which may be chewed, dissolved or swallowed or as powders, suspensions, optionally combined with various excipients, flavor enhancers or other compounds to enhance the texture of the composition.

It should be understood, of course, that the foregoing relates only to preferred embodiments of the present invention and that numerous modifications or alterations may be made therein without departing from the spirit and the scope of the invention.

What is claimed is:

1. In a topical composition for increasing hair growth comprising saw palmetto, the improvement comprising the inclusion of pharmaceutically effective amount of acetyl carnitine, co-enzyme Q10, and a pharmaceutically effective amount og a penetrating agent, wherein hair growth is increased.

2. The composition of claim 1, further comprising an effective amount of a preservative, an anti-microbial, a gelling agent, and an aroma improving agent.

3. The composition of claim 1, wherein the penetrating agent is selected from the group consisting of ethoxydiglycol, ethanol, Tween®80, lecithin organogel and PLURONIC® lecithin organogel.

4. A method of increasing hair growth comprising the step of topically administering a pharmaceutically effective amount of a composition comprising saw palmetto, co-enzyme Q10, acetyl carnitine and a penetrating agent, wherein the penetrating agent is selected from the group consisting of ethoxydiglycol, ethanol, Tween®80, lecithin organogel and PLURONIC®lecithin organogel.

5. The method of claim 4, wherein an increase in luster, and a decrease in sebum productions results, and hair looks healthier. penetrating agent is selected from the group consisting of ethoxydiglycol, ethanol, Tween®80, lecithin organogel and PLURONIC® lecithin organogel.

6. The method of claim 4 wherein the amount of saw palmetto is about 0.25 g to 20 g per 100 g of formulation, the amount of co-enzyme Q10 is about 0.1 g to 20 g per 100 g of formulation, and the amount of acetyl camitine is about 0.1 g to 20 g per 100 g of formulation.

7. The method of claim 4, wherein said composition is administered as a solution, lotion, cream, micelle, spray, gel or roller stick.

* * * * *